(12) United States Patent
Helm et al.

(10) Patent No.: US 12,064,193 B2
(45) Date of Patent: Aug. 20, 2024

(54) SELECTED IMAGE ACQUISITION TECHNIQUE TO OPTIMIZE SPECIFIC PATIENT MODEL RECONSTRUCTION

(71) Applicant: Medtronic Navigation, Inc., Louisville, CO (US)

(72) Inventors: Patrick A. Helm, Milton, MA (US); Shuanghe Shi, Southborough, MA (US)

(73) Assignee: Medtronic Navigation, Inc., Lafayette, CO (US)

(*) Notice: Subject to any disclaimer, the term of this patent is extended or adjusted under 35 U.S.C. 154(b) by 0 days.

(21) Appl. No.: 17/555,884

(22) Filed: Dec. 20, 2021

(65) Prior Publication Data
US 2022/0110696 A1 Apr. 14, 2022

Related U.S. Application Data

(60) Continuation of application No. 16/842,355, filed on Apr. 7, 2020, now Pat. No. 11,213,357, which is a
(Continued)

(51) Int. Cl.
*A61B 34/20* (2016.01)
*A61B 5/055* (2006.01)
(Continued)

(52) U.S. Cl.
CPC .............. *A61B 34/20* (2016.02); *A61B 5/055* (2013.01); *A61B 6/032* (2013.01); *A61B 6/4441* (2013.01);
(Continued)

(58) Field of Classification Search
CPC ......... A61B 34/20; A61B 5/055; A61B 6/032; A61B 6/4441; A61B 6/4476; A61B 6/461;
(Continued)

(56) References Cited

U.S. PATENT DOCUMENTS

| 4,042,811 | A | * | 8/1977 | Brunnett | ................. | A61B 6/032 |
| | | | | | | 250/369 |
| 5,448,607 | A | | 9/1995 | McKenna | | |

(Continued)

FOREIGN PATENT DOCUMENTS

| CN | 1143898 A | 2/1997 |
| CN | 1923138 A | 3/2007 |

(Continued)

OTHER PUBLICATIONS

"Medtronic O-Arm Multi-Dimensional Surgical Imaging System"; Brochure, 24pp, 2009.
(Continued)

*Primary Examiner* — Kathleen Y Dulaney
(74) *Attorney, Agent, or Firm* — Harness, Dickey & Pierce, P.L.C.

(57) ABSTRACT

A system and a method are disclosed that allow for generation of a model or reconstruction of a model of a subject based upon acquired image data. The image data can be acquired in a substantially mobile system that can be moved relative to a subject to allow for image acquisition from a plurality of orientations relative to the subject. The plurality of orientations can include a first and final orientation and a predetermined path along which an image data collector or detector can move to acquire an appropriate image data set to allow for the model of construction.

18 Claims, 9 Drawing Sheets

Related U.S. Application Data continuation of application No. 15/231,019, filed on Aug. 8, 2016, now Pat. No. 10,617,477, which is a continuation of application No. 14/319,202, filed on Jun. 30, 2014, now Pat. No. 9,412,200, which is a division of application No. 12/908,195, filed on Oct. 20, 2010, now Pat. No. 8,768,029.

(51) Int. Cl.
| | |
|---|---|
| A61B 6/00 | (2024.01) |
| A61B 6/03 | (2006.01) |
| A61B 6/46 | (2024.01) |
| A61B 34/10 | (2016.01) |
| A61B 90/00 | (2016.01) |
| G06T 11/00 | (2006.01) |
| G06T 17/10 | (2006.01) |

(52) U.S. Cl.
CPC ............ *A61B 6/4476* (2013.01); *A61B 6/461* (2013.01); *A61B 6/467* (2013.01); *A61B 6/487* (2013.01); *A61B 6/52* (2013.01); *A61B 6/5235* (2013.01); *A61B 34/10* (2016.02); *G06T 11/005* (2013.01); *G06T 17/10* (2013.01); *A61B 2034/105* (2016.02); *A61B 2034/2051* (2016.02); *A61B 2034/2055* (2016.02); *A61B 2090/0818* (2016.02); *A61B 2090/363* (2016.02); *A61B 2090/367* (2016.02); *A61B 2090/376* (2016.02); *A61B 2090/3764* (2016.02); *A61B 2090/3983* (2016.02); *A61B 2090/3995* (2016.02); *G06T 2211/412* (2013.01)

(58) Field of Classification Search
CPC ........... A61B 6/467; A61B 6/487; A61B 6/52; A61B 6/5235; A61B 34/10; A61B 2034/105; A61B 2034/2051; A61B 2034/2055; A61B 2090/0818; A61B 2090/363; A61B 2090/367; A61B 2090/376; A61B 2090/3764; A61B 2090/3983; A61B 2090/3995; G06T 11/005; G06T 17/10; G06T 2211/412
USPC ............. 382/131, 218, 284; 606/130; 378/1; 381/131
See application file for complete search history.

(56) References Cited

U.S. PATENT DOCUMENTS

| | | | |
|---|---|---|---|
| 5,689,629 A | 11/1997 | Lee | |
| 5,960,054 A | 9/1999 | Freeman et al. | |
| 6,320,929 B1 | 11/2001 | Von Der Haar | |
| 6,363,163 B1 | 3/2002 | Xu et al. | |
| 6,435,714 B1 | 8/2002 | Bruder | |
| 6,442,229 B1 | 8/2002 | Koehler et al. | |
| 6,681,129 B2 | 1/2004 | Matsuzaki et al. | |
| 6,697,508 B2 | 2/2004 | Nelson | |
| 6,862,335 B2 | 3/2005 | Basu et al. | |
| 6,904,163 B1 | 6/2005 | Fujimura et al. | |
| 6,909,792 B1* | 6/2005 | Carrott | G06T 7/0012 382/128 |
| 6,990,170 B2 | 1/2006 | Sugihara et al. | |
| 7,317,819 B2 | 1/2008 | Janes | |
| 7,518,619 B2 | 4/2009 | Stoval, III et al. | |
| 7,677,802 B2 | 3/2010 | Haras | |
| 7,881,423 B2* | 2/2011 | Tsuyuki | A61B 6/032 378/207 |
| 7,889,841 B2 | 2/2011 | Kargar et al. | |
| 7,942,829 B2 | 5/2011 | Miller et al. | |
| 8,046,052 B2 | 10/2011 | Verard et al. | |
| 8,055,046 B2 | 11/2011 | Feilkas et al. | |
| 8,086,299 B2 | 12/2011 | Adler et al. | |
| 8,238,631 B2 | 8/2012 | Hartmann et al. | |
| 8,325,873 B2 | 12/2012 | Helm et al. | |
| 8,768,029 B2 | 7/2014 | Helm et al. | |
| 8,831,303 B2 | 9/2014 | Villain et al. | |
| 9,014,780 B2 | 4/2015 | Wieczorek et al. | |
| 9,412,200 B2 | 8/2016 | Helm et al. | |
| 9,642,588 B2 | 5/2017 | Goto et al. | |
| 10,617,477 B2 | 4/2020 | Helm et al. | |
| 2002/0040220 A1 | 4/2002 | Zvuloni et al. | |
| 2002/0181752 A1 | 12/2002 | Wallo et al. | |
| 2003/0130576 A1 | 7/2003 | Seeley et al. | |
| 2003/0220557 A1 | 11/2003 | Cleary et al. | |
| 2004/0013225 A1* | 1/2004 | Gregerson | A61B 6/4405 378/19 |
| 2004/0022350 A1* | 2/2004 | Gregerson | A61B 6/4405 378/15 |
| 2004/0086076 A1 | 5/2004 | Nagaoka et al. | |
| 2004/0215071 A1* | 10/2004 | Frank | A61B 6/463 600/407 |
| 2004/0252873 A1 | 12/2004 | Avinash et al. | |
| 2004/0264625 A1 | 12/2004 | Basu et al. | |
| 2005/0027194 A1 | 2/2005 | Adler et al. | |
| 2005/0054915 A1 | 3/2005 | Sukovic et al. | |
| 2005/0068317 A1 | 3/2005 | Amakai | |
| 2005/0075563 A1 | 4/2005 | Sukovic et al. | |
| 2005/0113651 A1 | 5/2005 | Wood et al. | |
| 2005/0203385 A1 | 9/2005 | Sundar et al. | |
| 2005/0281387 A1* | 12/2005 | Kusch | A61B 6/00 378/197 |
| 2006/0002630 A1 | 1/2006 | Fu et al. | |
| 2006/0002631 A1 | 1/2006 | Fu et al. | |
| 2006/0084868 A1 | 4/2006 | Park | |
| 2006/0184016 A1 | 8/2006 | Glossop | |
| 2006/0247521 A1 | 11/2006 | McGee | |
| 2006/0291710 A1 | 12/2006 | Wang et al. | |
| 2007/0003117 A1* | 1/2007 | Wheeler | G06T 7/0012 382/128 |
| 2007/0014448 A1 | 1/2007 | Wheeler et al. | |
| 2007/0041660 A1 | 2/2007 | Mahesh et al. | |
| 2007/0071294 A1 | 3/2007 | Mahesh | |
| 2007/0104309 A1 | 5/2007 | Schonborn et al. | |
| 2007/0153972 A1 | 7/2007 | Fujishige et al. | |
| 2007/0167806 A1* | 7/2007 | Wood | A61B 6/032 600/459 |
| 2008/0009674 A1 | 1/2008 | Yaron | |
| 2008/0029704 A1* | 2/2008 | Hefetz | A61B 6/4266 250/363.01 |
| 2008/0147086 A1* | 6/2008 | Pfister | A61B 34/20 606/130 |
| 2008/0152205 A1 | 6/2008 | Vaillant et al. | |
| 2008/0260095 A1 | 10/2008 | Sukovic et al. | |
| 2008/0273779 A1 | 11/2008 | Pekar | |
| 2008/0281181 A1 | 11/2008 | Manzione et al. | |
| 2008/0287777 A1 | 11/2008 | Li et al. | |
| 2009/0060121 A1 | 3/2009 | Ziegler et al. | |
| 2009/0080737 A1 | 3/2009 | Battle et al. | |
| 2009/0092225 A1 | 4/2009 | Boese et al. | |
| 2009/0141854 A1 | 6/2009 | Hirokawa et al. | |
| 2009/0262886 A1 | 10/2009 | Mollus et al. | |
| 2010/0042011 A1 | 2/2010 | Doidge et al. | |
| 2010/0046817 A1* | 2/2010 | Goedicke | G01T 1/17 378/62 |
| 2010/0114308 A1 | 5/2010 | Maschke | |
| 2010/0128838 A1 | 5/2010 | Ayala et al. | |
| 2010/0172541 A1 | 7/2010 | Homan et al. | |
| 2010/0254509 A1* | 10/2010 | Sugaya | A61B 6/032 378/16 |
| 2010/0260404 A1 | 10/2010 | Ohishi | |
| 2010/0290690 A1 | 11/2010 | Hartmann et al. | |
| 2011/0125011 A1 | 5/2011 | Wieczorek et al. | |
| 2011/0172526 A1 | 7/2011 | Lachaine et al. | |
| 2011/0211744 A1 | 9/2011 | Darrow et al. | |
| 2012/0099679 A1 | 4/2012 | Yamada et al. | |
| 2014/0313193 A1 | 10/2014 | Helm et al. | |

(56) References Cited

U.S. PATENT DOCUMENTS

2014/0314203 A1 10/2014 Helm et al.
2014/0314296 A1 10/2014 Helm et al.

FOREIGN PATENT DOCUMENTS

| CN | 103260518 A | 8/2013 |
|---|---|---|
| CN | 103260519 A | 8/2013 |
| DE | 10237347 A1 | 3/2004 |
| DE | 102007037996 A1 | 2/2009 |
| EP | 2629667 A1 | 8/2013 |
| JP | 10033522 | 2/1998 |
| JP | 2003-153082 A | 5/2003 |
| JP | 2005-212131 A | 8/2005 |
| JP | 2005-536288 A | 12/2005 |
| JP | 2007-061426 A | 3/2007 |
| JP | 2007524445 A | 8/2007 |
| JP | 2007-319482 A | 12/2007 |
| JP | 2009-511430 A | 3/2009 |
| JP | 2009201840 A | 9/2009 |
| JP | 2009-545358 A | 12/2009 |
| JP | 2011507584 A | 3/2011 |
| WO | 9521570 A1 | 8/1995 |
| WO | 2004069053 A1 | 8/2004 |
| WO | 2004114220 A1 | 12/2004 |
| WO | 2008015611 A2 | 2/2008 |
| WO | 2009083866 A1 | 7/2009 |
| WO | 2010041201 A1 | 4/2010 |
| WO | 2012/054338 A1 | 4/2012 |
| WO | 2012/054737 A1 | 4/2012 |
| WO | 2012054338 A1 | 4/2012 |
| WO | 2012/177867 A2 | 12/2012 |

OTHER PUBLICATIONS

Chinese Office Action mailed Feb. 2, 2015 for China Patent Application No. 2015012800649060.
Chinese Office Action mailed Oct. 30, 2014 for China Patent Application No. 201180061196.X.
International Preliminary Report on Patentability and Written Opinion mailed May 2, 2013 for PCT/US2011/057118 claiming benefit of U.S. Appl. No. 12/908,195, filed Oct. 20, 2010.
International Search Report and Written Opinion mailed Feb. 7, 2012 for PCT/US2011/057118, claiming benefit of U.S. Appl. No. 12/908,195, filed Oct. 20, 2010.
International Search Report and Written Opinion mailed Mar. 9, 2012 for PCT/US2011/056372 claiming benefit of U.S. Appl. No. 12/908,186, filed Oct. 20, 2010.
Invitation to Pay Additional Fees mailed Dec. 27, 2011 for PCT/US2011/056372 claiming benefit of U.S. Appl. No. 12/908,186, filed Oct. 20, 2010.
Japan Office Action mailed Feb. 18, 2014 for Japan Patent Application No. JP2013-534973.
Japanese Office Action for JP Application No. 2015-054800 dated Feb. 16, 2016 with English translation.
Japanese Office Action for JP Application No. 2015-076150 dated Feb. 23, 2016 with English translation.
Japanese Office Action mailed Feb. 25, 2014 for Japanese Application No. JP2013-535093 filed Apr. 19, 2013, claiming benefit of PCT/US2011/057118, filed Oct. 20, 2011, claiming benefit from U.S. Appl. No. 12/908,195, filed Oct. 20, 2010.
Partial European Search Report dated Feb. 2, 2017 for EP Application No. 161680947 corresponding to PCT/US2011/056372 claiming benefit of U.S. Appl. No. 12/908,186, filed Oct. 20, 2010.
Priority Document D6, Granted U.S. Appl. No. 12/908,195, filed Oct. 20, 2010, U.S. Pat. No. 8,768,029 issued Jul. 4, 2014.
Third Office Action mailed Nov. 6, 2015 for Chinese Patent Application No. 201180061196.X.
Office Action mailed May 16, 2019 in corresponding/related European Application No. 16168094.7.
U.S. Appl. No. 16/842,355, U.S. Pat. No. 11,213,357, filed Apr. 7, 2020, Helm et al.
U.S. Appl. No. 15/231,019, U.S. Pat. No. 10,617,477, filed Aug. 8, 2016, Helm et al.
U.S. Appl. No. 14/319,202, U.S. Pat. No. 9,412,200, filed Jun. 30, 2014, Helm et al.
U.S. Appl. No. 12/908,195, U.S. Pat. No. 8,768,029, filed Oct. 20, 2010, Helm et al.
Second Office Action mailed Jun. 2, 2015 for Chinese Patent Application No. 201180061196.X.
Summons to attend oral proceedings pursuant to Rule 115(1) EPC dated Feb. 6, 2017 for European Application No. 117790337 corresponding to PCT/US2011/057118 claiming benefit of U.S. Appl. No. 12/908,195, filed Oct. 20, 2010.
European Office Action mailed Jun. 19, 2018 in corresponding European Application No. 18157524.2.

* cited by examiner

SELECTED IMAGE ACQUISITION TECHNIQUE TO OPTIMIZE SPECIFIC PATIENT MODEL RECONSTRUCTION

CROSS-REFERENCE TO RELATED APPLICATIONS

This application is a continuation of U.S. patent application Ser. No. 16/842,355 filed on Apr. 7, 2020, which is a continuation of U.S. patent application Ser. No. 15/231,019 filed on Aug. 8, 2016, which is a continuation of U.S. patent application Ser. No. 14/319,202 filed on Jun. 30, 2014, now U.S. Pat. No. 9,412,200 issued on Aug. 9, 2016, which is a divisional of U.S. patent application Ser. No. 12/908,195 filed on Oct. 20, 2010, now U.S. Pat. No. 8,768,029 issued on Jul. 1, 2014. The disclosure of the above applications are incorporated herein by reference

FIELD

The present disclosure relates to imaging a subject, and particularly to determining and performing an optimal movement of an imaging device relative to the subject and constructing a model of the subject.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g. C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

According to various embodiments, a method of acquiring image data of a subject with an imaging system is disclosed including positioning an imaging system relative to a region of interest, which can be encompassed by at least a portion of a human subject. The imaging system can include a detector to detect emitted energy, such as X-rays, from a source. The source and the detector can be provided generally opposite or opposed to one another in a gantry. A rotor can be positioned in the gantry that moves the source and the detector within the gantry. Moving the detector generally includes moving the source at a fixed position relative to the detector to maintain the opposed positioning. The method can further include positioning the gantry in a predetermined first orientation relative to the human subject based upon known possible movements of the gantry and a detector within the gantry to acquire a selected image data set of the human subject and moving at least one of the gantry and the detector to a predetermined final orientation relative to the human subject while acquiring image data of the human subject to acquire the selected image data set of the human subject. A three-dimensional model of the portion of the human subject regarding which the image data was acquired can be constructed based on the image data and the three-dimensional model can be displayed. The image data acquired of the human subject with the imaging system can include two-dimensional projections of the subject. These projections are acquired by detection of X-rays from the source. The three-dimensional model can be a three-dimensional volumetric model derived and/or generated from the acquired image data. Two dimensional projections can also be generated of the model which are line integrals of a three-dimensional object or model.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
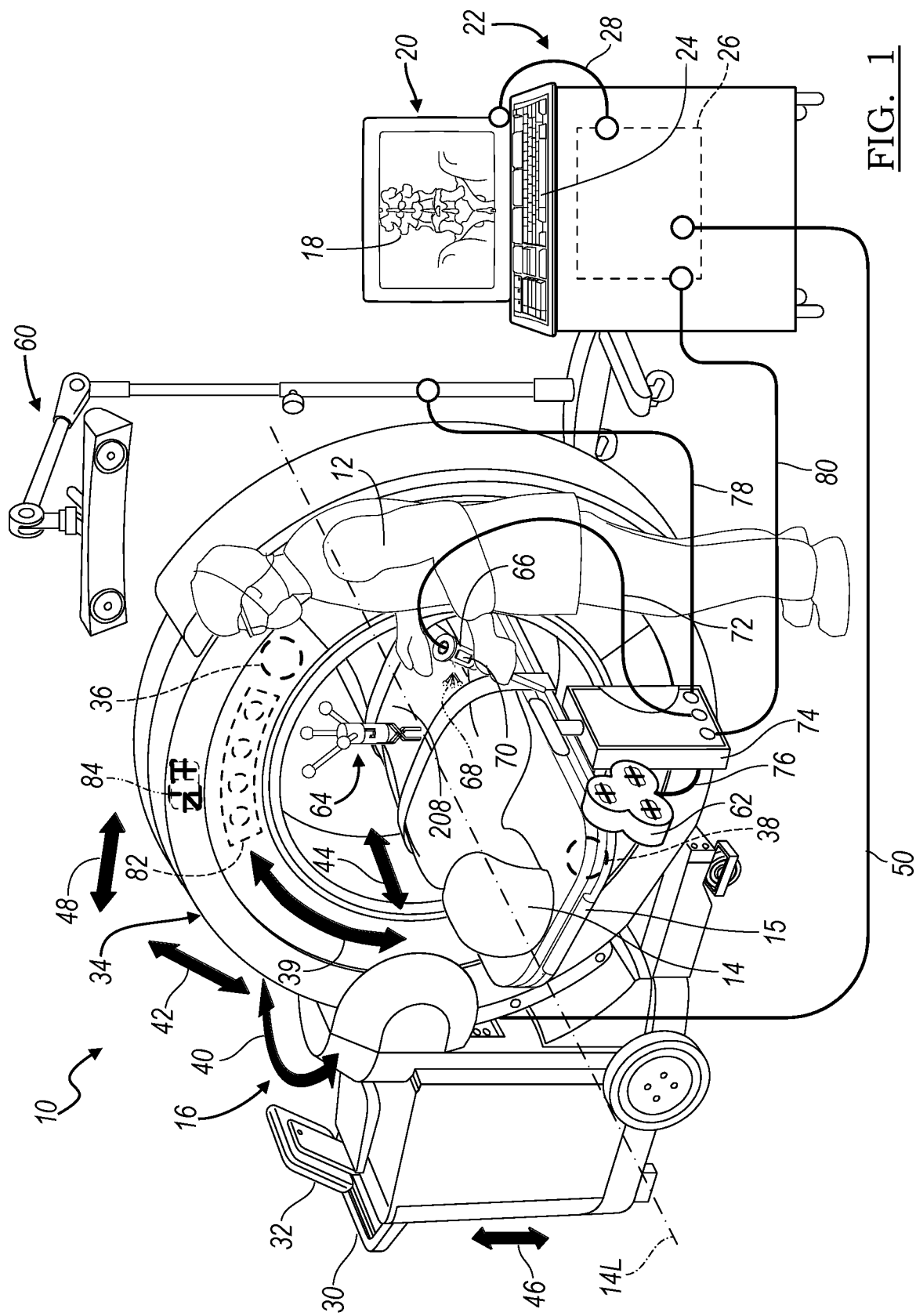
FIG. 1 is an environmental view of an imaging system in an operating theatre.

With reference to FIG. 1, in an operating theatre or operating room 10, a user, such as a surgeon 12, can perform a procedure on a patient 14. In performing the procedure, the user 12 can use an imaging system 16 to acquire image data of the patient 14 for performing a procedure. The image data acquired of the patient 14 can include two-dimension (2D) projections acquired with a X-ray imaging system, including those disclosed herein. It will be understood, however, that 2D forward projections of a volumetric model can also be generated, also as disclosed herein.

A model can be generated using the acquired image data. The model can be a three-dimension (3D) volumetric model generated based on the acquired image data using various techniques, including algebraic iterative techniques, also as discussed further herein. Displayed image data 18 can be displayed on a display device 20. The displayed image data 18 can be a 2D image, a 3D image, or a time changing four-dimension image. The displayed image data 18 can also include the acquired image data, the generated image data, both, or a merging of both the types of image data.

It will be understood that the image data acquired of the patient 14 can be acquired as 2D projections, for example with a X-ray imaging system. The 2D projections can then be used to reconstruct the 3D volumetric image data of the patient 14. Also, theoretical or forward 2D projections can be generated from the 3D volumetric image data. Accordingly, it will be understood that image data can be either or both of 2D projections or 3D volumetric models.

The display device 20 can be part of a processor system 22 that includes an input device 24, such as a keyboard, and one or more processors 26 (the one or more processors can include multiple-processing core processors, microprocessors, etc.) that can be incorporated with the processing system 22. A connection 28 can be provided between the processor 26 and the display device 20 for data communication to allow driving the display device 20 to illustrate the image data 18.

The imaging system 16 can include an O-Arm® imaging system sold by Medtronic Navigation, Inc. having a place of business in Louisville, CO, USA. The imaging system 16, including the O-Arm® imaging system, or other appropriate imaging systems in use during a selected procedure are also described in U.S. patent application Ser. No. 12/465,206 filed on May 13, 2009, incorporated herein by reference.

The O-Arm® imaging system 16 includes a mobile cart 30 that includes a control panel or system 32 and an imaging gantry 34 in which is positioned a source unit 36 and a detector 38. The mobile cart 30 can be moved from one operating theater or room to another and the gantry 34 can move relative to the cart 30, as discussed further herein. This allows the imaging system 16 to be mobile allowing it to be used in multiple locations and with multiple procedures without requiring a capital expenditure or space dedicated to a fixed imaging system.

The source unit 36 can emit x-rays through the patient 14 to be detected by the detector 38. As is understood by one skilled in the art, the x-rays emitted by the source 36 can be emitted in a cone and detected by the detector 38. The source/detector unit 36/38 is generally diametrically opposed within the gantry 34. The detector 38 can move rotationally in a 360° motion around the patient 14 generally in the directions of arrow 39 within the gantry 34 with the source 36 remaining generally 180° from and opposed to the detector 38. Also, the gantry 34 can isometrically sway or swing (herein also referred to as iso-sway) generally in the direction of arrow 40, relative to the subject 14, which can be placed on a patient support or table 15. The gantry 34 can also tilt relative to the patient 14 illustrated by arrows 42, move longitudinally along the line 44 relative to the patient 14 and the cart 30, can move up and down generally along the line 46 relative to the cart 30 and transversely to the patient 14, and move perpendicularly generally in the direction of arrow 48 relative to the patient 14 to allow for positioning of the source/detector 36/38 relative to the patient 14. The O-Arm® imaging device 16 can be precisely controlled to move the source/detector 36/38 relative to the patient 14 to generate precise image data of the patient 14. The imaging device 16 can be connected with the processor 26 via connection 50 which can include a wired or wireless connection or physical media transfer from the imaging system 16 to the processor 26. Thus, image data collected with the imaging system 16 can be transferred to the processing system 22 for navigation, display, reconstruction, etc.

Briefly, according to various embodiments, the imaging system 16 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. The navigated space or navigational domain relative to the patient 14 can be registered to the image data 18 to allow registration of a navigation space defined within the navigational domain and an image space defined by the image data 18. A patient tracker or dynamic reference frame 64 can be connected to the patient 14 to allow for a dynamic registration and maintenance of registration of the patient 14 to the image data 18.

An instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74 as can the electromagnetic localizer 62 and/or the optical localizer 60. Using the communication lines 74, 78 respectively, the probe interface 74 can then communicate with the processor 26 with a communication line 80. It will be understood that any of the communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, neurological stent or the like. The instrument 66 can be an interventional instrument such as a deep brain or neurological stimulator, an ablation device, or other appropriate instrument. Tracking the instrument 66 allows for viewing the instrument's 66 location relative to the patient 14 with use of the registered image data 18 and without direct viewing of the instrument 66 within the patient 14.

Further, the imaging system 16 can include a tracking device, such as an optical tracking device 82 or an electromagnetic tracking device 84 to be tracked with a respective optical localizer 60 or electromagnetic localizer 62. The tracking device can be associated directly with the source 36, the detector 38, the gantry 34, or other appropriate part of the imaging system 16 to determine the location or position of the detector relative to a selected reference frame. As illustrated, the tracking device can be positioned on the exterior of the housing of the gantry 36. Accordingly, the imaging device 16 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206.

Figure 2:
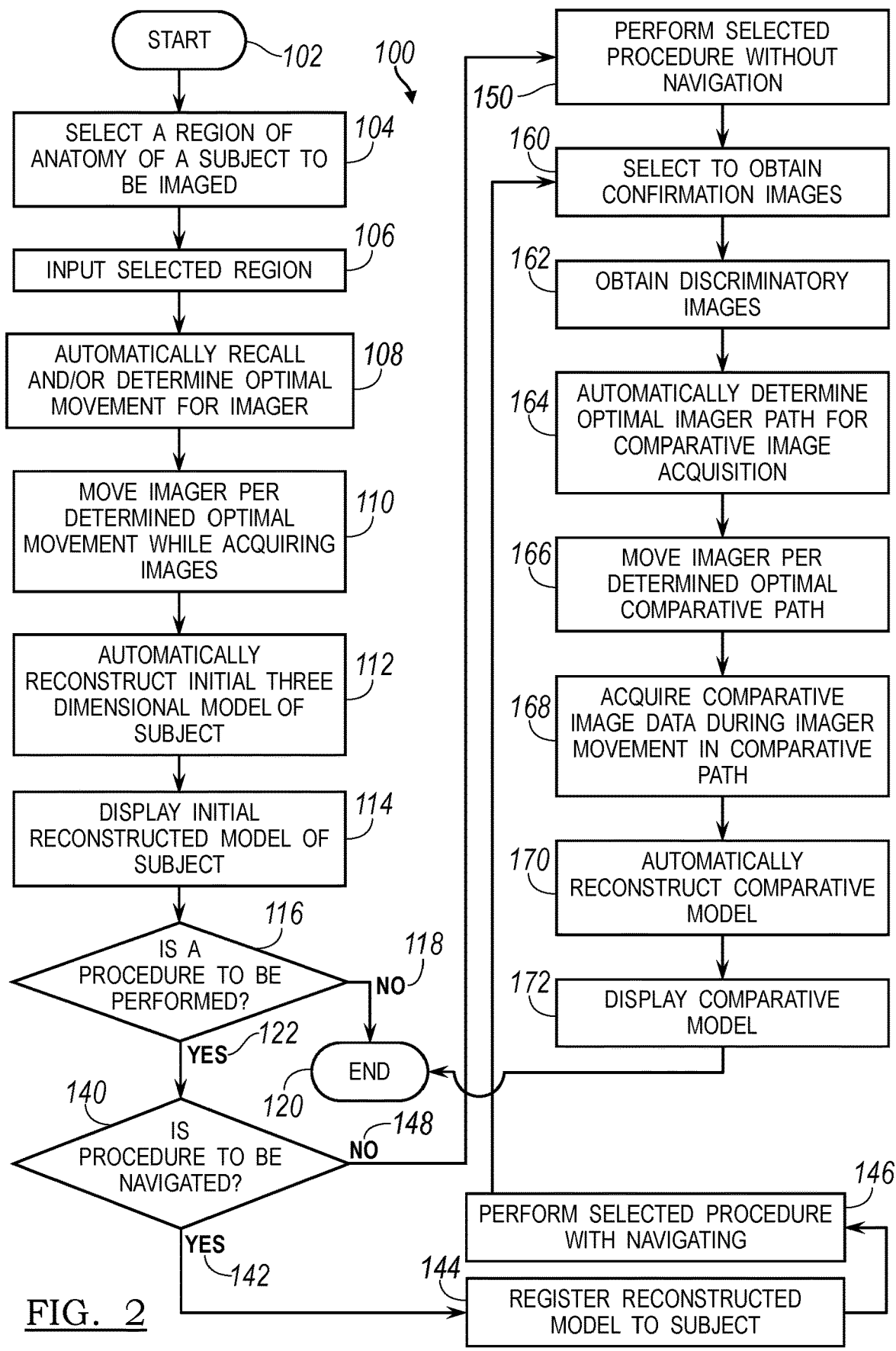
FIG. 2 is a flowchart of a procedure for acquiring image data of a subject for rendering a model of the subject.

With reference to FIG. 2, a flowchart 100 illustrates an exemplary procedure of acquiring image data with the imaging system 16 and performing a procedure with the acquired image data and a selected reconstruction and verifying/confirming/determining a success of the selected procedure. The flowchart 100 can begin in start block 102 and proceed to select a region of an anatomy of a subject to be imaged in block 104. Selecting the appropriate region of the subject can include selecting a region of the patient 14 for imaging. For example, if a spinal implant is to be positioned in a lumbar region, then selecting a lumbar region of the patient to be imaged can be made. Similarly, if a brain or neuro procedure is to be performed, the brain or the head of a patient 14 can be imaged. In like manner a pelvis, legs, or any other appropriate portion of an anatomy of the subject 14 can be imaged.

Once the region is selected, the region can be inputted in block 106. After inputting the region, an optimal movement of the imaging system 16 can be automatically determined and/or recalled in block 108. Movement of the imaging system 16 can include movement of the source 36 and the detector 38 generally 360° around a longitudinal axis 14L of the patient 14 and movement of the gantry 34 relative to the patient 14, including the isometric sway angular movement 40, tilt movement 42, longitudinal movement 44, and other movements of the gantry 34 relative to the patient 14. Movement of the detector 38 alone or with movement of the gantry 34 can move the detector 38 and the source 36 relative to the patient 14 to acquire image data at a plurality of selected locations and orientations relative to the subject 14.

The optimal movement can be based on acquiring adequate image data to generate an initial three dimension model in block 112. The model can be generated, as discussed below, with the image data acquired during movement of the imaging system along the optimal path. The optimal path can be one that allows an appropriate image data collection with minimal radiation usage or exposure. The image data collection can be optimized to acquire image data with minimal, but appropriate overlap of data collection. Also, the optimization can allow for the collection of sequential/step image collection or continuous image collection during the image data collection. Regardless, the optimal path is automatically executed by the imaging system to collect the appropriate amount of image data during the path.

Also, the optimal path can differ from a manual path in acquiring image data at only predetermined locations of the detector relative to the patient 14. This will allow for the usage of only minimal radiation dosages to acquire the image data by collecting minimal, but appropriate amounts of image data of the patient. The path can be designed to move in non-circular motions relative to the patient 14 to achieve the image data collection and at selected times during the path from a beginning or initial position to a final position.

After automatically determining optimal movement in block 108, the imaging system 16 can be moved according to the optimal movement in block 110. Image data can be acquired of the patient 14 while moving the source/detector 36/38 which can be used, such as with transfer to the processor 26 or stored in any appropriate storage media, for analysis and reconstruction. Automatic reconstruction of an initial three dimensional model of the subject can be then be performed in block 112. Reconstruction of the three dimensional model can be performed in any appropriate manner, such as using an algebraic techniques for optimization.

Appropriate algebraic techniques include Expectation maximization (EM), Ordered Subsets EM (OS-EM), Simultaneous Algebraic Reconstruction Technique (SART) and total variation minimization, as generally understood by those skilled in the art. The application to performing a 3D volumetric reconstruction based on the 2D projections allows for efficient and complete volumetric reconstruction.

Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. The theoretical model can be associated with theoretical image data to construct the theoretical model. In this way, the model or the image data 18 can be built based upon image data acquired of the patient 14 with the imaging device 16.

The 2D projection image data can be acquired by substantially annular or 360° orientation movement of the source/detector 36/38 around the patient 14 due to positioning of the source/detector 36/38 moving around the patient 14 in the optimal movement. Also, due to movements of the gantry 34, the detector need never move in a pure circle, but rather can move in a spiral helix, or other rotary movement about or relative to the patient 14. Also, the path can be substantially non-symmetrical and/or non-linear based on movements of the imaging system 16, including the gantry 34 and the detector 38 together. In other words, the path need not be continuous in that the detector 38 and the gantry 34 can stop, move back the direction from which it just came (e.g. oscillate), etc. in following the optimal path. Thus, the detector 38 need never travel a full 360° around the patient 14 as the gantry 34 may tilt or otherwise move and the detector 38 may stop and move back in the direction it has already passed.

The reconstructed model can then be displayed on the display device 20 in block 114. As discussed above, the imaging system 16 can be used to generate image data or allow for reconstruction of a model of the patient 14 or portion of the patient 14 relating to the selected region in block 104 substantially in the operating theatre 10. Accordingly, the imaging device 16 can be used immediately prior to or during an operative procedure. Also, the imaging device 16 can be moved from one operating theater to another with the cart 30 that has wheels or is otherwise mobile. This can reduce requirements of operating rooms dedicated to imaging or having a fixed imaging system.

Because the imaging system 16 can be used during or before a procedure, a decision block can be used to determine whether procedures are to be performed in block 116. If no procedure is to be performed then NO path can be followed to end block 120. It will be understood that the displayed reconstructed model can be viewed by the user 12 or any appropriate person or technician for analyzing the patient 14. The reconstructed model can be used to for analysis, diagnosis or planning as appropriately selected. If a procedure is to be performed, a YES path 122 can be followed to a second decision block 140 to determine whether the procedure is to be navigated.

If the procedure is to be navigated, a YES path 142 can be followed to register the reconstructed model to an appropriate reference frame (such as the dynamic reference frame 64) associated with the subject in block 144. Registration can be performed in any appropriate manner such as identifying landmarks or fiducials on the patient 14 and related marks in the image data 18. The registration can be substantially automatic, inherent by positioning the patient 14 at a known location relative to the imaging device 16, or manually. Once registration is achieved, registration can be maintained with the dynamic reference frame 64 connected to the patient 14 and tracked with the appropriate tracking system using the selected localizer 60, 62. Once registered, a procedure can be navigable performed in block 146.

If it is selected to not perform a navigated procedure, then a NO path 148 can be followed to perform a selected procedure without navigation in block 150. If no navigation is required, the localizer 60, 62 need not be used to track instruments and the reconstructed image model can be used to determine a particular procedure or for analysis in selecting an appropriate implant or the like.

Once the procedure has been performed, it can be selected to obtain confirmation images in block 160. The confirmation images can be used to confirm the procedure was completed satisfactorily, according to a predetermined plan, etc. The confirmation images can be equal in amount, less, or more than the image data acquired in block 110. After selecting to obtain confirmation images in block 160, discriminatory images can be obtained in block 162. The discriminatory images can be selected limited number of images of the patient 14 at discrete positions relative to the patient 14.

After acquiring or obtaining the discriminatory images in block 162, an optimal path for the imager for acquiring comparative images can automatically be determined in block 164. A procedure of obtaining the discriminatory images in block 162 and automatically determining an optimal comparative imager path for comparative images in block 164 will be described in further detail herein. Determining the optimal comparative path can include avoiding regions of collision. This can include a user inputting or the system can recall positions of positioned instruments and avoid colliding with these in the optimal path. The items that may cause collision need not necessarily be surgical instruments, but can be other items in the operating theater. Nevertheless, once the optimal comparative path for acquiring the comparative images is determined, the imager can be moved along the optimal comparative path in block 166 and comparative image data can be acquired during movement in the optimal comparative path in block 168.

An automatic reconstruction of a post procedure 3D reconstructed model, also referred to herein as a comparative model, using the comparative image data to compare to the initial reconstructed model can be performed in block 170. The post procedure or comparative model is based on image data, such as 2D projections, acquired of the patient 14 after a portion of or all of the procedure has been performed. The comparative model can be reconstructed using a similar algebraic iterative technique that can be used to generate the new or the initial pre-procedure 3D volumetric reconstructed model based only on comparing the comparative image data to the initial three dimensional model, as discussed further herein. The comparative model can then be displayed on an appropriate display device, including the display device 20, in block 172 and the procedure can then end in block 120.

Thus, it will be understood that the flowchart 100 can be used for different or multiple procedures including automatically determining an optimal path for an initial patient image acquisition and model reconstruction that can end in block 120. However, it can also be determined to perform a procedure and allow for navigation of a procedure with the initial reconstructed model from block 112. The procedure can be navigated or not navigated and after the procedure, a confirmation or verification can be performed using comparative image data acquired with the imaging device 16 to image the patient 14 to view the results of the performed procedure. The method can then end in block 120 after performing the procedure and performing a comparison or generating a comparative model with the image data.

Figure 3:
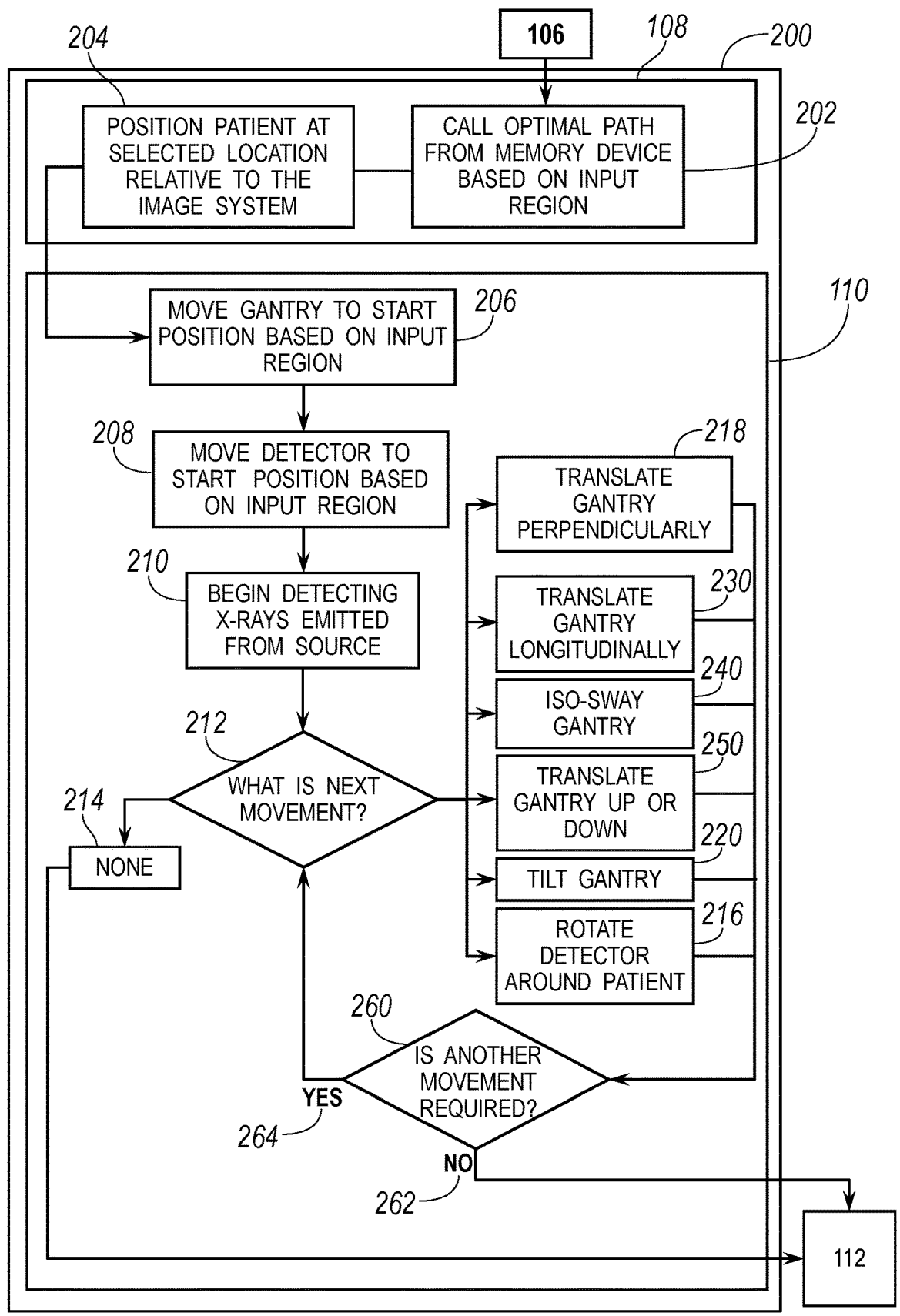
FIG. 3 is a flowchart showing an expanded portion of the flowchart in FIG. 2.

The flowchart 100 illustrates a procedure or method that can begin with acquiring images of a patient, reconstructing a model of the patient, performing a procedure, and confirming or verifying a procedure with additional imaging. As discussed above, automatically determining an optimal movement of the imager in block 108 can include various steps or procedures. As illustrated in FIG. 3 in a flowchart 200 of a method, procedures for determining the optimal movement of the imager in block 108 are illustrated in the flowchart 200. The flowchart 200 can be understood to be an expansion of blocks 108 and 110 in flowchart 100. Accordingly, block 106, which includes inputting the selected region, can begin the method 200. Then the method 200 can end by flowing into block 112 to reconstruct the initial three dimensional model of the subject 14. Accordingly, the flowchart 200 can be understood to be a part of the flowchart 100 expanded and illustrated in detail.

Once the region is selected in block 106, the flowchart 200 can begin with block 202 by calling an optimal path from a memory device based on the input region. Calling the optimal path can include accessing a memory system that can be included in the cart 30, associated with a processor 26, or at any other appropriate location. The optimal path 202 can be based upon preacquired or predetermined knowledge of general or standard anatomy of the subject, such as a human patient, the geometry of the imaging system 16, the possible movements of the imaging system 16, and other criteria to obtain a selected or optimal image data of the subject 14 based upon the input region in block 106. For example, the optimal path can include an appropriate beginning or initial location of the detector 38 relative to the patient 38, movements of the detector 38 and the gantry 34 relative to the patient 14, and a final location of the detector 38 relative to the patient 14. The path can be to achieve an appropriate image data collection to allow for the initial three dimension reconstruction in block 112 of the selected region of the patient 14.

The optimal path can be based upon testing and analysis of image data acquisition of the patient 14 or patients prior to a current patient 14. The analysis can be based upon test image data acquired of various patients and a plurality of patients. Statistical and other analysis can then be applied to the image data to determine optimal location for positioning the detector 38 relative to the patient to image at the selected region. A path of movement of the detector 38 can then be determined within the movement range of the imaging device to acquire the optimal image data at the determined locations. Generally, the optimal path will allow for the acquisition of an appropriate amount of image data to allow for a true or appropriate three dimensional reconstruction of the patient 14 with minimal exposure to radiation from the source 36. Regardless of the method for determining the optimal path, the optimal path can be called in block 202 to determine or input movements of the imaging system 16 relative to the patient 14.

The optimal path can be used to acquire enough image data to form or reconstruct the initial three-dimensional image model of the patient 14 in block 112, but with limited patient exposure to radiation or image acquisition time. The optimal path will include both a path of movement and a timing and number of image data positions to be acquired. Thus, the detector 38 can be instructed to move relative to the patient 14 in the selected path and either stop to acquire image data or collect image data at a selected rate.

The optimal path will, therefore, acquire an appropriate amount of image data with substantially only a necessary overlap of image positions that allows for the model reconstruction. This can limit radiation exposure and eliminate manual movement of the imaging system, either with a controller or with physical power, to acquire the image data. The optimal path in acquiring the image data for reconstruction can be used to ensure that enough image data perspectives of the patient 14 are acquired for the reconstruction with minimal undersampling or unnecessary over sampling of different perspectives. Also, the movement of the imaging system in combination with the optimal path can ensure that the detector 38 is able to reach all of the optimal imaging positions.

The patient 14 can be positioned at a selected location relative to the imaging system in block 204, this position can be based on the called optimal path form block 202. Positioning the patient 14 relative to the imaging system 16 can include positioning the patient on the operating bed or support 15 and can further include securing the patient with securing straps or members 208 to the patient support 15. Further, positioning the patient 14 relative to the selected imaging system 16 can include positioning the patient 14 at a selected position relative to the gantry 34 so that the input selected region from block 106 is positioned at a selected position relative to the cart 30 or other position of reference for the imaging system. The gantry 34 is able to move due to the mechanical connections to the gantry 34 to the cart 30 relative to the cart 30 and the optimal path can be referenced to a reference point of the cart 30. Thus, the patient 14 or other subject can be positioned relative to the reference position of the cart 30 so that the optimal path can be achieved relative to the reference position. For example, if a lumbar region is to be imaged the patient can be positioned such that the L1 vertebra is aligned with a reference point of the cart 30 and about 15 cm from the reference point. It will be understood that the reconstruction can occur with selected amounts of interpolation based on small differences in varying patient anatomy and positioning of the patient 14.

Additionally, the detector 38 is positioned on a rail or track system within the gantry 34 and is able to rotate around a center defined relative to the annular gantry 34 and therefore the detector 38 also moves relative to the cart 30. Accordingly, the patient 14 is moved to a position relative to the imaging system 16, including the cart 30, which allows the detector 38 to be positioned at a selected position relative to the patient 14 to allow for acquisition of image data according to the optimal path called in block 202. Again, the patient 14 can be moved relative to a reference point relative to which the optimal path is selected and the detector 38 can be instructed to follow the optimal path once the patient 14 is positioned in the selected position in block 204.

Once the patient 14 is positioned in the selected location relative to the imaging system in block 204, the gantry 34 can be moved to a start position in block 206 and the detector 38 can be moved to a start position in block 208. It will be understood that the imaging system 16 may have a park or stationary orientation that may include a standard or set start position that does not require the gantry 34 or the detector 38 to move to a specific start position for each optimal path, but instead is a standard imaging system start position. Nevertheless, the optimal path may include a selected optimal start position, which can be achieved by moving the gantry 34 to a start position in block 206 and moving the detector 38 to a start position in block 208.

Further, it will be understood that moving the detector 38 also includes moving the source 36, which is substantially diametrically opposed to the detector 38 across the patient 14 and the gantry 34. As discussed above, and understood by one skilled in the art, the source 36 can be an x-ray source. The detector 38 is generally positioned directly opposed to the source 36 on an opposite side of the subject to be imaged, such as the patient 14. Discussion herein of movement of the detector 38, therefore generally, includes inherent movement of the source 36 to ensure that a beam of x-rays passes through the patient 14 in an appropriate manner to be detected by the detector 38.

After the gantry 34 and the detector 38 are moved to the start position in blocks 206, 208 respectively, block 210 can include detecting x-rays emitted from the source 36. As understood by one skilled in the art, once detection begins, image data acquisition also begins. Accordingly, if the detector 38 is positioned opposed to the source 36, with the patient 14 in the beam of the x-rays, then image data is detected by the detector of the patient 14. After the x-rays begin being emitted and detected in block 210, decision block 212 allows for determining what the next movement is. If only a single image position is required or determined by the optimal path in block 202, then a none decision path 214 can be followed. If the none decision path 214 is followed, then the processor can exit the flowchart 200 and move to the reconstruction block 112 from the flowchart 100.

Generally, however, movement of the gantry 34 and/or the detector 38 may be selected to achieve multiple orientations of the detector 38 relative to the patient 14 to allow for a more complete or better reconstruction of a model of the patient 14. In particular, when reconstructing a three dimensional model it may be selected to acquire a plurality of orientations or positions of the detector 38 relative to the patient 14 to allow for the three dimensional reconstruction. In particular, it may be selected to move the detector 38 at least 360° around the patient 14 to allow for detection of x-rays and therefore image data, at a complete 360° circle around the patient 14 and therefore 360° around the region input in block 106. Although, movement of the detector 38 need not be circular, but can be spiral, etc., as discussed above.

The movement of the detector 38, however, may be generally stepwise or sequential or continuous and image data acquisition may also follow this process. In other words, the detector 38 may be allowed to continually or substantially continually (e.g. about 10 millisecond detector refresh-rate) collect image data of the patient 14 as the detector moves in the optimal path. Alternatively, or in addition to the continuous collection, the detector 38 may be moved from one optimal location to another and only collect limited image data at the selected locations to generate a more step-wise image data acquisition.

Accordingly, the decision block 212 of what the next movement is can generally lead to at least one of five movement choices. It will be understood that the imaging system 16 can move in any appropriate manner and those discussed here are exemplary of movement of the O-Arm® imaging system. Regardless, a first type of movement can include rotational movement of the detector 38 around the patient in block 216. As exemplarily illustrated in FIG. 4A, rotation of the detector 38 can include movements of the detector 38 generally in the direction of arrow 39 in an annular or circular path around the gantry 34 of the imaging system 16. The patient 14 positioned within the imaging system 16 can be imaged with the x-rays by movement of the detector 38 relative to the patient 14 as the detector moves in the annular path 39. Motorized portions can move the detector 38 along the track within the gantry 34 at precise steps or substantially continuous movements as selected by the optimal path in block 202.

Figure 4A:
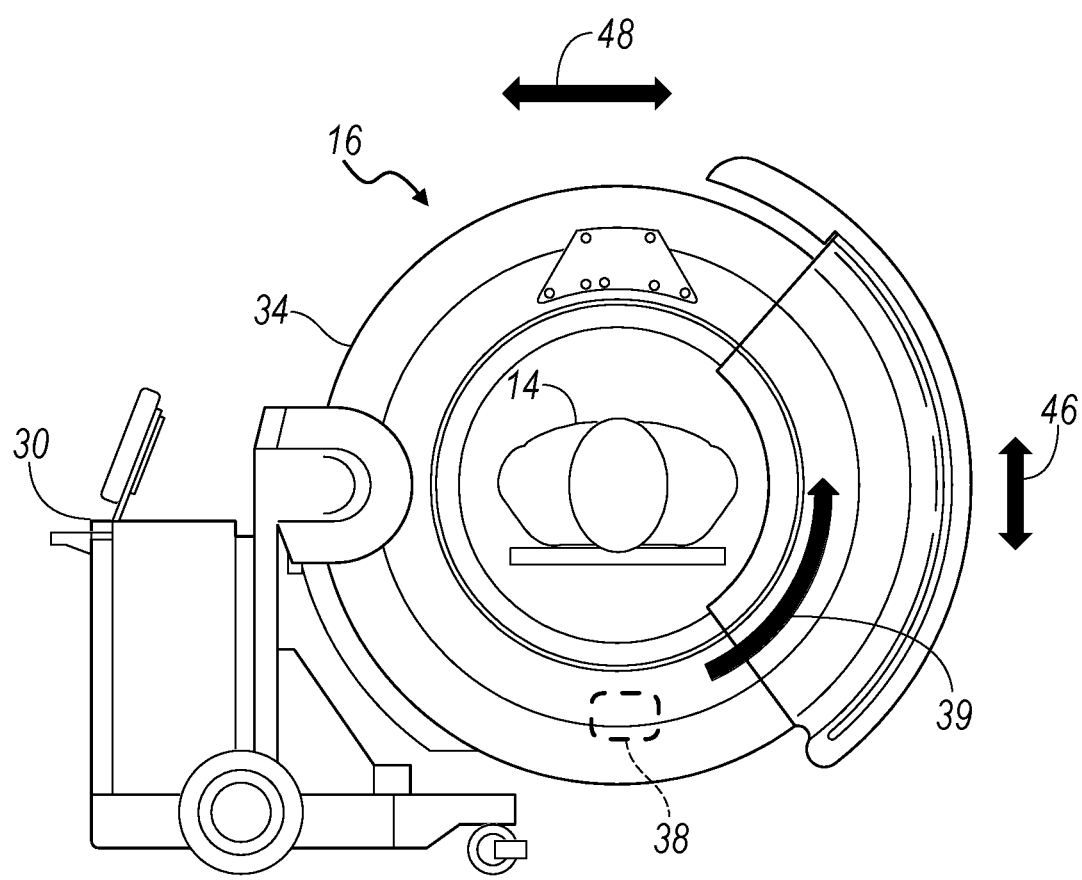
FIGS. 4A-4E illustrate possible movements of an imaging system.

Selected movements can include perpendicular movement of the gantry 34 in block 218 relative to the patient 14 and the cart 30 in the direction of arrow 48, as illustrated in FIG. 4A. The perpendicular movement of the gantry 34 allows the patient 14 to be positioned relative to the cart 30 on the patient support 15 with enough clearance for procedures or other instruments. The gantry 34 can then move to a selected position to move the detector 38 in the selected path, as discussed herein.

Figure 4B:
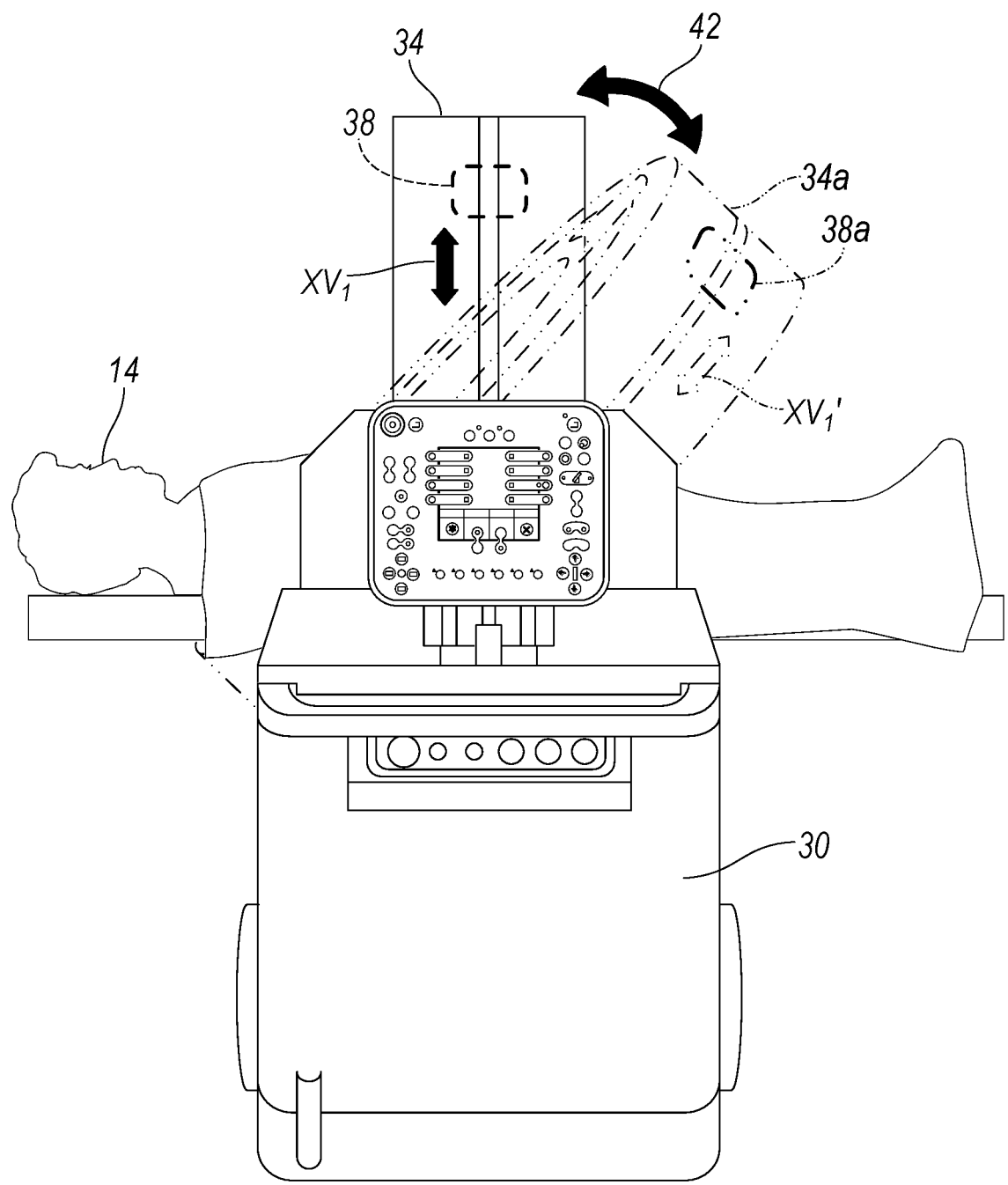

The gantry 34 can also be tilted, as illustrated in FIG. 4B relative to the patient 14 or the cart 30 generally in the direction of arrow 42 in block 220. Tilting of the gantry 34 allows for tilting of the beam of x-rays, illustrated by vector XV1 from a first position illustrated by a vector XV1 to a second position or orientation illustrated by a vector XV1' and the second orientation of the detector 38a in the tilted gantry 34a. Accordingly, the gantry 34 can tilt relative to the patient 14 to provide a selected orientation of the detector 38 relative to the patient 14. It will be understood that the gantry 34 can tilt either during or at a selected time in the path of the detector or movement of the detector 38 relative to the patient 14. Accordingly, the detector may move from a start position, as illustrated in FIG. 4A to a position approximately 90° rotated relative to the patient 14 and then the gantry 34 can tilt relative to the patient 14 and the detector 38 can either return the same 90°, move an additional arc in the same direction as previously moved, or return a portion of the arc previously traversed. It will be further understood that the detector 38 may rotate an entire 360° within the gantry 34 and then the gantry 34 can tilt and the detector 38 can return or move in a reverse direction within the gantry towards its initial starting position within the gantry, but along a different path defined now by the tilted gantry 34 relative to the patient 14.

Figure 4C:
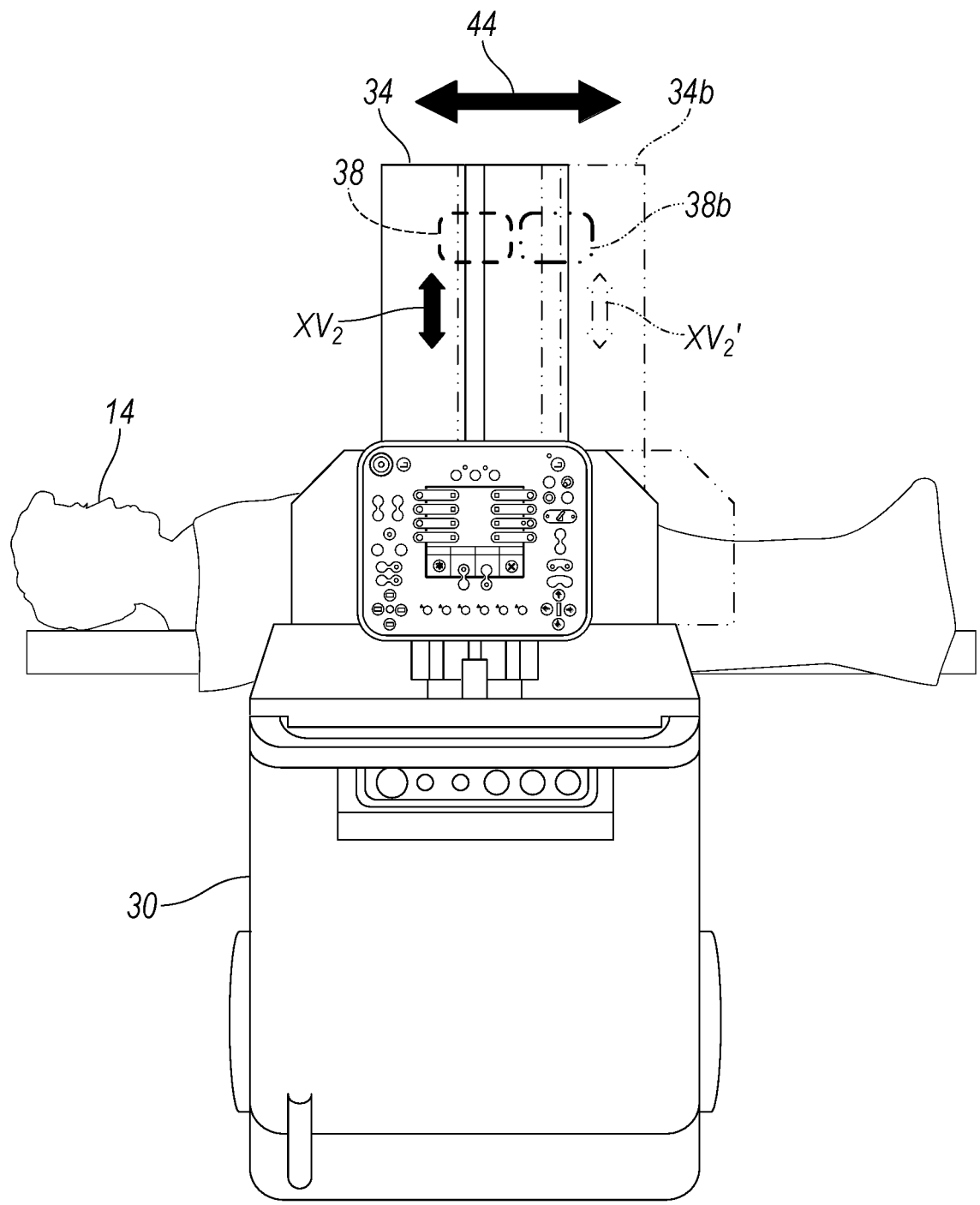

The gantry 34 can also translate longitudinally in block 230 as illustrated in FIG. 4C. The translation can generally be in the direction of arrow 44, as also illustrated in FIG. 1, which can generally be along the longitudinal axis of the patient 14L. Again, movement of the gantry 34 can be used to move the detector 38 from a first position or a selected position to a second selected position illustrated in phantom 38b. Thus, the gantry 34 can move from a first selected position 34 to a second selected position 34b and subsequently the direction or orientation of the x-ray beam can move from a first position, illustrated by a vector XV2 to a second position illustrated by vector XV2'.

Figure 4D:
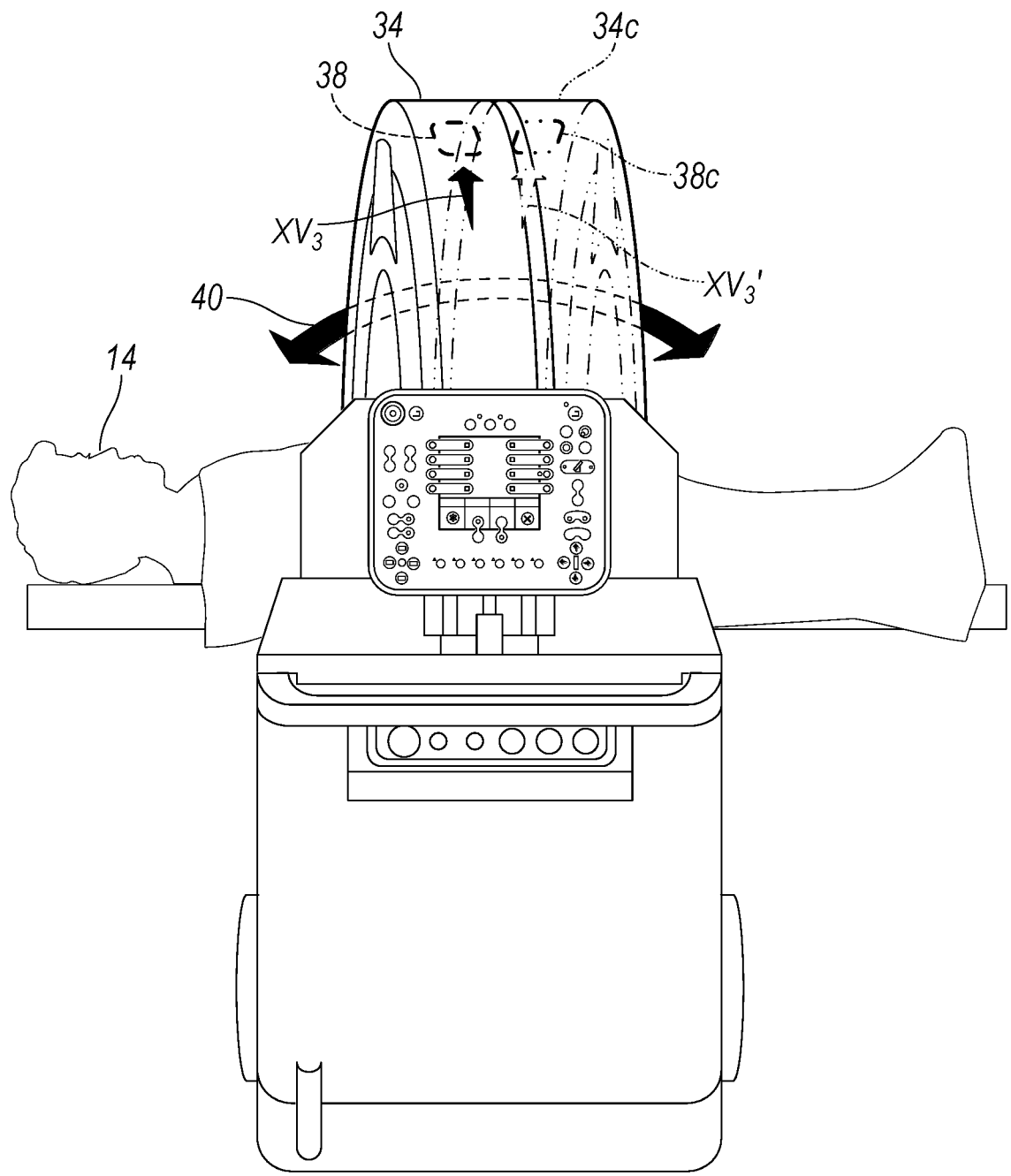

The gantry 34 can also iso-sway in block 240 as illustrated in FIG. 4D. The iso-sway of the gantry 34 can be generally in the direction of arrow 40, as also illustrated in FIG. 1. Iso-swaying the gantry 34 moves the gantry 34 in a portion of an arc around a line tangent to the gantry 34. Iso-swaying the gantry 34 can move the detector 38 from a first position, illustrated as 38 in FIG. 4D to a second position illustrated in phantom 38c in FIG. 4D. The iso-sway of the gantry 34 can allow for different orientations of the detector 38 relative to the patient 14 not allowed only by tilting the gantry 34 in block 220 as illustrated in FIG. 4B. Accordingly, the gantry 34 can also be iso-swayed relative to the patient 14 as illustrated in FIG. 4D to move the detector 38 and the respective x-ray vector relative to the patient 14.

Figure 4E:
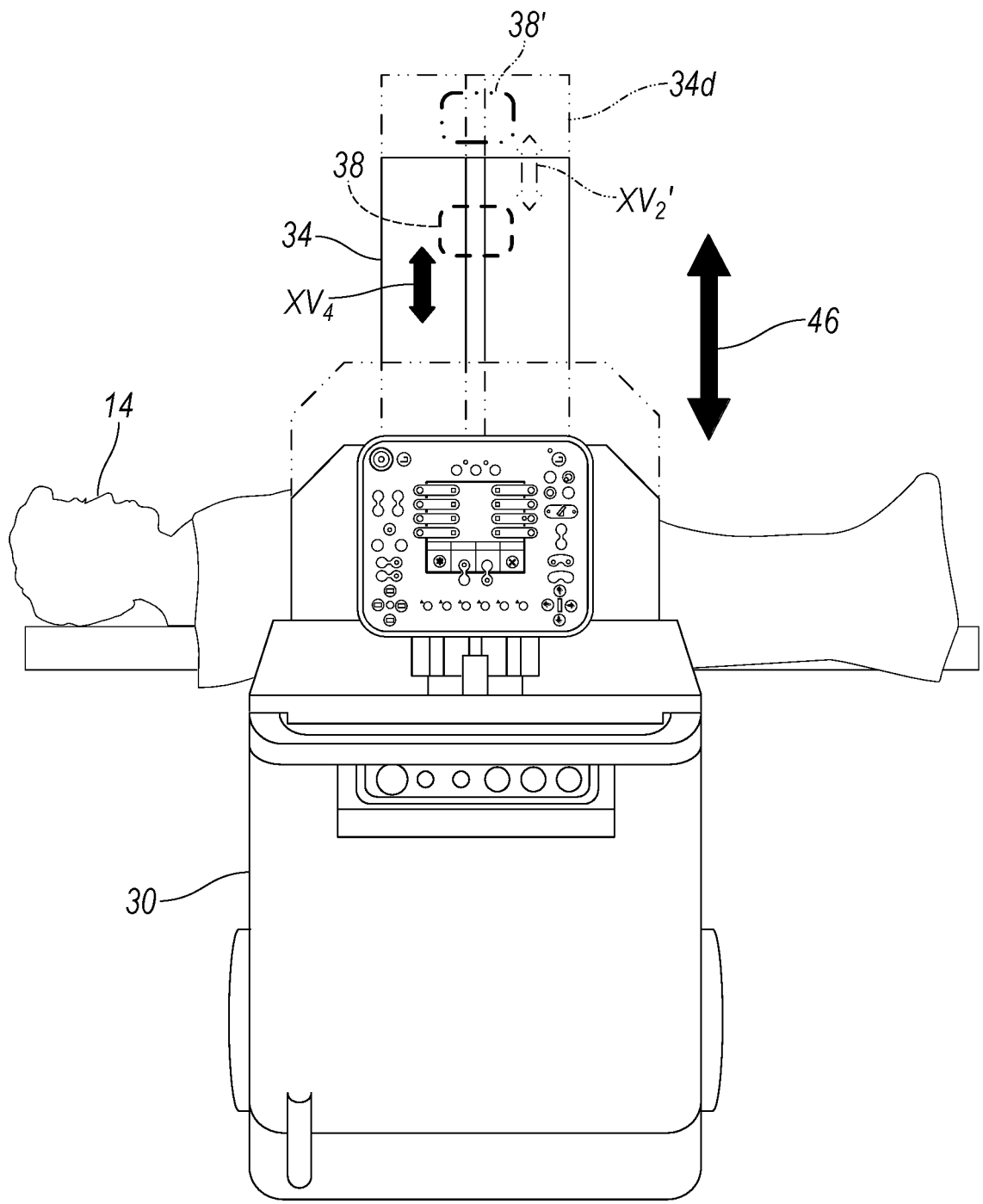

Finally, the gantry can be translated up and down in block 250 as illustrated in FIG. 4E. Moving the gantry 34 up and down relative to the cart 30 or the patient 14 can move the detector 38 from a first position, illustrated as 38 in FIG. 4E to a second position, illustrated in phantom 38' in FIG. 4E. Accordingly, the x-ray vector can move from a first position XV4 to a second position XV4 as the gantry is moved to a second position 34d'. Although the movement illustrated in FIG. 4E illustrates that the x-ray vector XV is generally still substantially perpendicular to a longitudinal axis of the patient 14, it will be understood that movement of the imaging system 16 can be combined.

Accordingly, movement of the gantry 34 up and down as illustrated or defined by movement in the direction of arrow 46 can be combined with iso-swaying in block 240 and tilting in block 220 to move the x-ray vector or beam vector relative to the patient 14 that is not allowed by simply tilting or iso-tilting the gantry 34. The coordinated movements of the gantry 34 and the detector 38 can cause longitudinal pivoting and other coordinated movements relative to the patient 14. The coordinated movements allow the gantry 34 and the detector 38 to move substantially simultaneously or effectively simultaneously to achieve movement in multiple axes during a movement relative to the patient 14.

Once the next movement is determined the movement can be achieved in one of the blocks 216, 218, 220, 230, 240, or 250. After the appropriate movement is determined or made in one of the respective movement blocks, a further decision block can be used to determine whether another movement is required in block 260. If no additional movement is required, then a NO path 262 can be followed to the reconstruction block 112 and follow the flowchart 100 discussed above.

It will be understood that certain optimal paths may only require a single movement from an original or starting position to achieve a selected data set acquisition. Further, it will be understood that translating a detector 216 can include a continuous translation or can include a certain amount of translation. Accordingly, if the movement selected in block 212 is translation of the detector 38, a single 360 degree sweep or scan can be made of the patient 14 and that can be the only movement required to acquire the image data or reconstruction in block 112.

Nevertheless, additional movements may be required, such as combination of different movements, therefore a YES path 264 can be followed back to the initial decision block 212 to determine what the next movement is. The next movement can be included in the optimal path called in block 202 and can include additional movements, such as a selected tilt or translation or can include moving the gantry 34 after translating the detector 38 a selected amount. For example, as discussed above, the detector 38 can translate a certain arc length, such as about 90°, and then the gantry 34 can be tilted in block 220 a selected amount, such as about 5° from its last position, thus allowing the detector 38 to translate at a different orientation relative to the patient 14. Accordingly, the determination of whether another movement is required in block 260 can be used to move the detector 38 and substantially complex orientations and movements relative to the patient 14 to acquire an optimal image data set according to the optimal path in block 202.

The imaging system can move relative to the patient 14 in a selected amount which can be used to identify or determine the optimal path which can be called in block 202. Movement of the imaging system 16 can include a substantially 360° rotation or translation of the detector 38 relative to the patient 14. Additionally, tilt movement of the gantry 34 can be about 30 degrees)(° to about 60°, including about 40° to about 50°, and further including about 45° either direction of a line normal to the longitudinal axis 14L of the patient. The gantry 34 can also have a total longitudinal translation movement of about 10 centimeters (cm) to about 30 cm, including about 15 cm to about 20 cm, and including about 17.8 cm. The gantry 34 can have an isotilt of about 5° to about 20°, and further about 10° to about 15° and further about 12° either direction of a line substantially normal to the longitude axis 14L of the patient 14. Finally, the gantry 34 can have a total up and down movement of about 20 cm to about 70 cm, about 40 cm to about 50 cm, and further about 45.7 cm.

Any of the possible movements can be combined to move the detector 38 at any selected position relative to the patient 14 required by the optimal path. The optimal path called in block 202, however, can be based upon the region inputted in block 106 and can be substantially standardized for a selected type of subject, such as a human patient. Thus, the optimal path can be standardized based on analysis, image data acquired at various positions of the detector, etc. for a human patient. For example, to allow for a reconstruction of a vertebra the optimal path can include obtaining two orthogonal images in a first plane, tilting the gantry 34 collecting two additional orthogonal images at different locations, then isotilting the gantry 34 and repeating. The movements of the imaging system 16 can be used to ensure an appropriate perspective relative to the patient 14 and the optimal path can be used to ensure that the optimal number of image data locations are acquired for each patient.

The optimal path, in accessing it for acquiring the image data, can be used to limit radiation and power usage to only a minimal or optimal amount for image data collection. Further, a technician or user of the imaging system 16 need not guess or determine positions for image data acquisition for each new patient. This can reduce procedure time and training. In other words, a completely manual system may require the user to ensure positioning of the patient 14 relative to the detector 38 is proper for each image and can overcompensate for limitations in knowledge of the imaging system 16 by over acquiring the image data and, thus, possibly using more power and radiation than necessary. Also, the optimal path can ensure that enough image data is acquired for the model reconstruction with a minimal number of image data acquisition positions or radiation usage. Thus, over- or under-sampling can be avoided.

The optimal path can be stored and accessed substantially quickly during a procedure to allow for the acquisition of an image data set substantially immediately prior to the performing of a procedure for the particular type of subject, such as the human patient 14. It will be understood, that substantially immediately prior to performing of a procedure can include the time after the operating theater 12 has been prepared for the procedure and the patient 14 is also prepared for the procedure and either the operating surgeon is in the operating theatre 12 or preparing to enter the operating theater 12. Thus, the image data acquired of the patient 14 is substantially immediately before performing the procedure and generally in the same room or operating theater.

Figure 5:
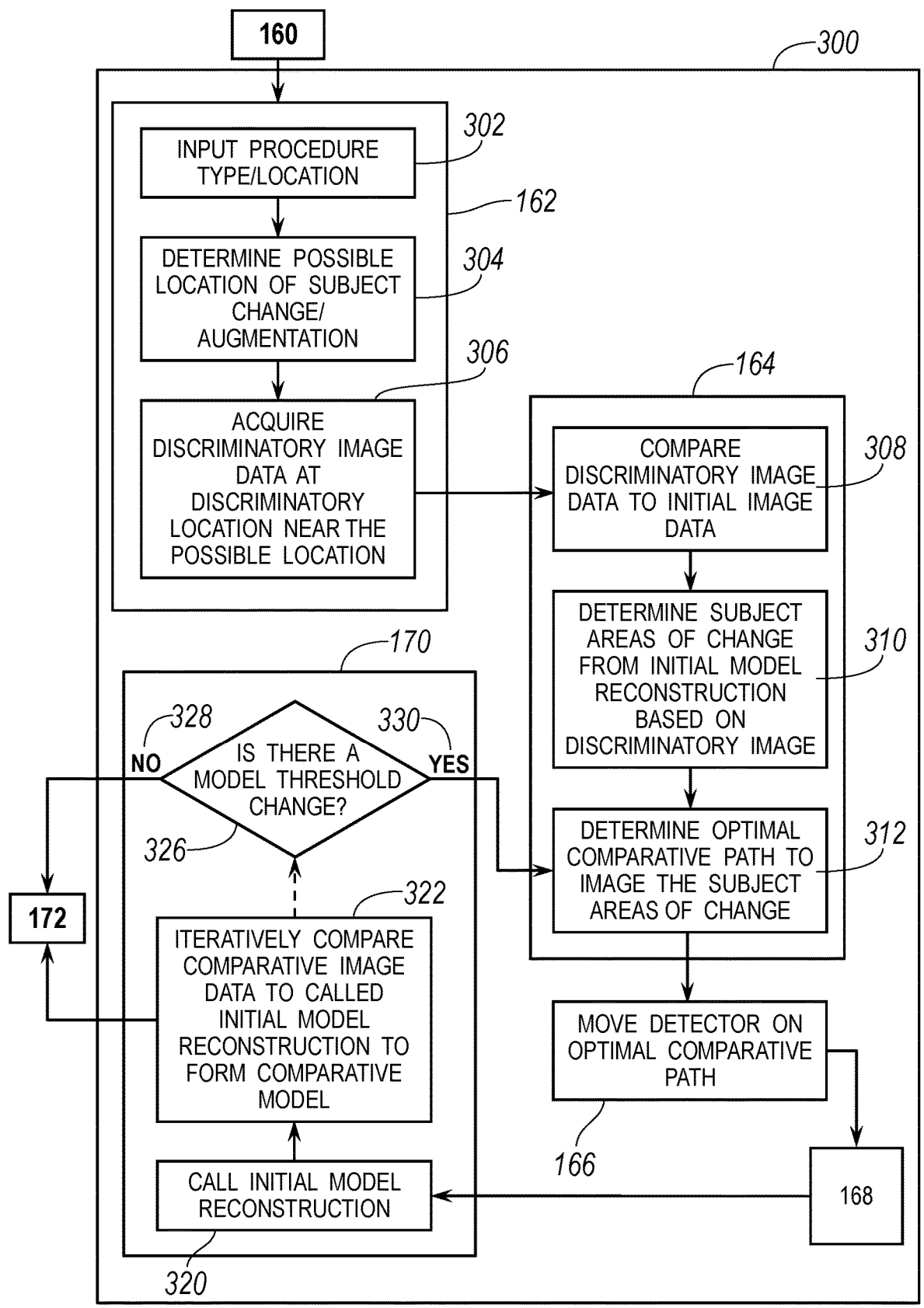
FIG. 5 is a flowchart showing an expanded portion of the flowchart in FIG. 2.

The flow chart 100 illustrated in FIG. 2, as briefly discussed above, illustrates a method for automatically acquiring image data, forming an initial reconstruction or model of the patient, performing a procedure, and performing the confirmation or verification procedure. The confirmation or verification procedure discussed above in flow chart 100 is illustrated in greater detail in flow chart 300 in FIG. 5. It will be understood that the procedure illustrated in flow chart 300 can be included in the flow chart 100 discussed above. It is described in greater detail here for understanding of a confirmation or verification procedure according to various embodiments.

After performing a selected procedure, it can be selected to obtain confirmation or verification images for a comparative reconstruction in block 160. Once this selection has been made to obtain verification images or to reconstruct the verification or comparative model, an input of the procedure type or location can be made in block 302. The input of the location or type of procedure in block 302 can be manually input by the user 12 after performing the procedure or could be called or recalled from the region initially selected in block 104, or determined by performing a navigated procedure in block 146. It will be understood that the navigated procedure can include inputs regarding the type of implant, region of the anatomy of the patient 14, or other information that can be used to determine the type or location of the procedure for input in block 302. Accordingly, the input of procedure type or location in block 302 can be manually input at a selected time by the user 12, or any other appropriate individual, or can be automatically determined or recalled based upon previous inputs.

With or without the procedure or location input in block 302, a determination of possible locations of change or augmentation to the subject 14 can be made in block 304. The determination of possible location are subject to change or augmentation in block 304 can be based upon known movement of the patient 14 based upon the procedure performed in block 146 or 150, or can be input by the user 12 or other appropriate individual manually. For example, if the procedure is to implant a spinal implant, it may be known which vertebrae were affected and which vertebrae should be imaged for a comparative reconstruction. This determination can be made automatically by the processor 26, or other appropriate processor executing instructions based upon the input procedure, or based upon a manual input by the user 12 or other appropriate individual.

Also, if the procedure is a navigated procedure the processor can include input regarding the portion of the patient 14 on which a procedure is performed and/or which areas or volume of the initial model may be changed due to the tracked instrument relative to the registered image data. The patient 14 can be registered to the image data 18 displayed on the display 20. The image data 18 can include the initial 3D reconstructed model. Thus, the initial 3D model can be registered to the patient 14 and the location of the instrument 66 is tracked relative to the patient 14 and the image data 18. This, in turn, allows the processor system 26 to determine the location of the instrument 66, possible change of the patient 14, etc. This can be used as an input in block 304 to assist in determining an optimal comparative path in block 312. Additionally, geometry, anatomical effect, etc. of an implant or instrument can also be input or known to assist in determining possible areas of change in the patient 14.

Further, determining a possible location of subject change or augmentation can include both the direct portion of the anatomy affected by the procedure, such as the vertebrae to which an implant is attached or positioned, and also other anatomy that may be affected due to the procedure. For example, if a spinal implant is to re-position one vertebra relative to another vertebra, the other soft tissue or vertebrae beyond the ones directly implanted or connected with an implant may be affected due to movement of the anatomy of the patient 14. Accordingly, the determination of the location of subject change or augmentation can include both the direct area of a procedure and surrounding areas or other areas of the subject anatomy based upon determination of the user 12, previous inputs into the system, and other stored data.

Once the determination of subject change or augmentation has been made, acquisition of discriminatory image data can be acquired at discriminatory locations near the possible locations of change or augmentation in bock 306. The discriminatory images or image data can be discrete images that are acquired at spaced apart locations relative to the patient 14. As discussed above, the detector 38 can move relative to the patient according to the possible movements of the imaging system 16. However, to form a comparative reconstruction model, it can be selected to only image those portions of the patient 14 that have changed due to the procedure. Accordingly, the discriminatory images can be made relative to the patient 14 at discrete locations to determine those areas that should be imaged to allow for the reconstruction of the comparative model. The discrete images can include a small number of images, such as one, two, three or ten or any appropriate number of images that can be less than an entire number of images or discrete locations of the detector 38 required to form the initial or the comparative reconstructed model.

Once the discriminatory image data is acquired at the discrete locations of block 306, it can be compared to the initial three dimensional model reconstruction in block 308. For example, the discriminatory image data can be 2D projections that are acquired of the patient at selected locations. These can be compared to forward projections or theoretical projections from the initial 3D reconstructed model of the patient 14 at identical or substantially identical locations. Thus, the discriminatory image data acquired at a position relative to the patient 14 can be compared to substantially the identical forward projected position, even if one or more of the initial projections was not taken at the same position relative to the patient 14 as one or more of the discriminatory image projections. Also, the discriminatory images can be selected to be in substantially identical locations to at least some of the image data collection locations in block 110 so that the discriminatory images can be compared directly to the first images from block 110.

From the comparison, a determination of whether a change has occurred in the discriminatory image data greater than a threshold amount from the initial reconstructed model can be made. The threshold can be set at any appropriate level and can be selected for imaging speed, reconstruction speed, image acquisition or radiation dose, etc. Generally, however, the threshold will be used to determine if a discriminatory image is different from the initial model. The difference can be a statistical difference or percentage difference or variance in a pixel or voxel data (e.g. brightness, contrast, etc.). Thus, it will be understood, that the threshold need not be a set value for a particular image.

The comparison made in block 308 can assist in determining whether any discrete location at which discriminatory image data was acquired in block 306 includes differences from the initial reconstructed model. A determination of subject areas of change from the initial model reconstruction based on the discriminatory image data can then be made in block 310. The determination of subject areas of change in block 310 is based upon the comparison in block 308. For example, if a first discrete location at which a first discriminatory image data is acquired shows no or substantially no change (i.e. below the threshold level), then a determination of subject area of change can be determined to not have occurred at the first discrete location. It will be understood that the amount of change (e.g. the threshold) can be set at a particular threshold such as about 0.1% to about 10%, including about 2%, and further including about 1% change of the discriminatory image data compared to a projection based on the initial model. The amount of change can be based upon movement of portions of the anatomy or inclusion of implants, volume of anatomy in the area, or other appropriate thresholds. A determination can be made in block 310 if a change requiring additional images is found in the discriminatory images, that being that the amount of change found in the comparison shows an amount of change above the threshold.

After the determination of subject areas of change is made in block 310, a determination of an optimal comparative path to image the subject area of change can be made in block 312. The determination of an optimal path can be based upon the determined areas of subject change in block 310. For example, if ten discriminatory images are taken in block 306 and a determination that areas 3, 4, 5 and 6 show a change above the threshold, then the determination of an optimal comparative path can be made to image the area encompassing the discrete areas 3-6 of the total ten discriminatory images taken. Accordingly, the optimal path can be determined to be less than the automatically determined optimal path in block 108. If the comparative path is shorter or includes fewer acquired projections then the amount of radiation, time, movement, etc. needed to acquire the comparative images is generally less than to acquire the initial image data. It will be understood, however, that if the amount of change is great enough (e.g. a major reconstruction of the patient's 14 anatomy has occurred) then the determined optimal comparative path in block 312 can be substantially equal to or the same as the optimal path determined in block 108.

The determined optimal comparative path, however, can be based upon the specific location of a procedure and the amount of possible change done to the patient 14 during the procedure. The determined optimal comparative path can also include or account for knowledge or information regarding the procedure or implant positioned in the patient 14. For example, if a spinal disc implant is positioned in the patient or if a spinal fusion occurs, the geometry of the implant is known. The geometry of the implant can be used in determining an appropriate comparative path for acquiring comparative image data. The geometry of the implant can help in determine the distance changes of the anatomy based on dimensions and affects of the implant, amount of change, volume of the patient 14 affected, etc.

The discriminatory images acquired in block 306 can assist in determining whether or where the change is great enough to require the acquisition of additional images for forming a comparative reconstructed model. The optimal comparative path can also include a plurality of paths. In other words, several passes over a similar or identical portion of the patient 14 can be used to ensure appropriate sampling and appropriate orientation of the detector 38 relative to the patient 14 for image data acquisition. Accordingly, the comparative reconstructed model, as discussed further herein, can be based upon the initial reconstructed model in block 112 augmented only to show the change to the patient 14 due to the procedure and determined with the comparative image data.

Once the determined optimal comparative path is determined in block 312, the detector can be moved on the optimal comparative path in block 166. Comparative image data can then be acquired in block 168 as discussed above. The comparative image data will be the image data acquired while the detector is moved on the optimal comparative path determined in block 312. Again, the determined optimal comparative path can be determined substantially intraoperatively or substantially immediately post operatively based upon the discrete image data. Also, acquiring the image data in block 168 can be substantially different for each and every patient on which a procedure is performed based upon the amount of change, the type of implant used, the initial reconstructed model, and other parameters based on the specific patient 14 on which a procedure is being performed.

Once the comparative image data is acquired in block 168, a calling or recalling of initial model reconstruction can be performed in block 320. The initial model reconstruction from block 112 can be stored in an appropriate memory system that is associated with the processor 26 or separate from the processor 26, but can be recalled for comparing to the comparative image data from block 168. The comparison of the comparative image data in block 168 to the called initial model reconstruction can be performed in block 322. The comparative image data can be iteratively compared to the initial model reconstruction in block 322 to allow for a formation of a comparative model.

The comparative model formed in block 322 can be generated based upon the comparative image data and the initial model and can include less processing than forming the initial model. The lower processing can be due, at least in part, because the initial model should remain unchanged for the areas of the patient 14 unaffected by the procedure. Also, the known movement of the instruments 66 (i.e. from tracking the instruments) and/or geometry of implants can be used to assist in forming the comparative model. Thus, if the procedure, is not a drastic or overly invasive procedure the comparative reconstruction may require only processing of the areas of change of the patient 14. Although it will be understood that the areas of change can be substantial such that the comparative model can be substantially different than the initial model from block 112. In other words, the comparative model may be based substantially completely on a new image data set collected during collecting the comparative image data in block 168.

Also, acquiring the discrete images in block 306 and the comparative image data in block 168 can allow for the reduced x-ray exposure to the patient 14 and the user 12 and other individuals in the operating theater 10 by allowing for the determination of a small area of change, if possible, rather than reimaging the entire area or volume of the patient 14 used in block 112 to generate the initial reconstructed model. Accordingly, the radiation exposure of the patient 14 can be minimized based upon the procedure performed and the determined optimal comparative path in block 312. Nevertheless, the comparative model determined in block 322 can be used to verify or confirm the procedure performed on the patient 14, including a selected result being achieved or solution to the ailment of the patient 14 with the procedure.

The comparative model can be displayed at 172. However, either prior to or after forming the comparative model, a determination can be made of whether the comparative model is beyond the threshold change difference from the discriminatory image data acquired in block 306 or the initial model called in block 320 in determination block 326. As discussed above, the threshold can be a percentage change, an absolute amount, or other amount of change between the comparative model and the initial determined model in block 322 or compared to prior models or the image data. If no threshold change is determined, then a NO path 328 can be followed to block 172. However, if an amount of change greater than a threshold amount is determined, then a YES path 330 can be followed to block 312 to further determine an optimal path to acquire comparative image data. The amount of change or the threshold change can also refer to variance in the image data acquired during the acquisition of the comparative image data and comparative model generated or formed in block 322.

Thus, the generation of the comparative model can be an iterative process and allow the image data to be acquired in several steps. Accordingly, an initial optimal path can be determined in block 312 and a comparative image data model can be generated in block 322 based upon the single path and acquisition of data. If an amount of variance or change is determined between the comparative model and the initial model or the discriminatory image data, however, a second optimal comparative path can be determined to acquire additional image data at areas necessary to remove variances from the comparative image model. The reason for acquiring additional image data or selecting to acquire additional image data can include sampling rates of selected areas, movement of the patient, change to the patient, or other factors in acquiring enough image data to generate an appropriate comparative image data model in block 322.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An imaging system for acquiring image data of a subject, comprising:
    a mobile cart configured to move from a first location to a second location;
    a gantry movably attached to the mobile cart and configured to be positioned relative to a region of interest;
    a detector moveable with and relative to the gantry to acquire comparative image data; and
    a processor configured to execute instructions to:
        acquire initial image data of the region of interest by moving at least one of the gantry or the detector from a first position to a final position relative to the region of interest while acquiring a selected image data set of the region of interest via the detector;
        construct an initial three-dimensional model of at least a portion of the region of interest based on the acquired selected image data set;
        compare an acquired discriminatory discrete location image data to the constructed initial three-dimensional model of the portion of the region of interest;
        identify specific regions having a threshold change between the acquired discriminatory discrete location image data and the constructed initial three-dimensional model of the portion of the region of interest;
        determine at least one location of at least one of the detector or the gantry to acquire comparative image data regarding the specific regions having the threshold change;
        acquire the comparative image data at the determined at least one location of at least one of the detector and the gantry;
        construct a comparative model of the region of interest based on the constructed initial three-dimensional model and the acquired comparative image data; and display the constructed comparative model of the region of interest to illustrate changes to the region of interest;
wherein the gantry includes an annular inner wall and an annular outer wall that encloses a volume and the detector is configured to move within the volume;
wherein the detector is configured to move to the at least one location alone within the volume or with movement of the gantry;
wherein the detector is operable to move independent of the gantry and the gantry is operable to move independent of the mobile cart;
wherein the threshold change is about 0.1% to about 10%.

2. The system of claim 1, wherein the processor: further acquires the discriminatory discrete location image data of the region of interest at or near a known altered portion of the region of interest.

3. The system of claim 2, wherein constructing the comparative model of the region of interest after acquiring the discriminatory discrete location image data of the region of interest is based on a determined difference between the constructed initial three-dimensional model and the acquired comparative image data.

4. The system of claim 3, further comprising:
executing instructions with the processor system to determine a plurality of locations for movement of at least one of the detector or the gantry to acquire a plurality of comparative image data regarding a specific region having the threshold change;
wherein constructing the comparative model includes executing instructions with the processor system to determine differences between the initial three dimensional model and the comparative image data acquired.

5. The system of claim 4, wherein the plurality of locations includes an optimal path of movement of the detector relative to the region of interest.

6. The system of claim 1, wherein acquiring the comparative image data includes acquiring less image data than during acquisition of an initial image data set of the region of interest.

7. The system of claim 1, wherein the processor is configured to execute further instructions to identify the specific regions having the threshold change based at least on a tracked position of an instrument.

8. An imaging system for acquiring image data of a subject, comprising:
a mobile cart configured to move from a first location to a second location;
a gantry movably attached to the mobile cart and configured to be positioned relative to a region of interest;
a detector moveable with and relative to the gantry to acquire comparative image data; and
a processor configured to execute instructions to:
construct an initial three-dimensional model of at least a portion of the region of interest based on an acquired selected image data set of the region of interest;
compare an acquired discriminatory discrete location image data to the constructed initial three-dimensional model of the portion of the region of interest, wherein the acquired discriminatory discrete location image data includes less image data than the acquired selected image data set of the region of interest;
determine at least one location for positioning at least one of the detector or the gantry to acquire a comparative image data set regarding an identified region having a change between the acquired discriminatory discrete location image data and the constructed initial three-dimensional model based at least on the comparing an acquired discriminatory discrete location image data to the constructed initial three-dimensional model of the portion of the region of interest;
determine at least one path of movement of at least one of the gantry or the detector to reach the determined at least one location; and
acquire the comparative image data at the determined at least one location of at least one of the detector or the gantry after moving at least one of the gantry or the detector along the determined at least one path;
wherein the gantry including an annular exterior wall and an annular interior wall that encloses a volume and the detector is configured to move within the volume;
wherein moving the imaging system along the at least one path includes moving the detector alone within the volume or with movement of the gantry along the at least one path;
wherein the processor further determines a threshold for the change between the acquired discriminatory discrete location image data and the constructed initial three-dimensional model;
wherein the threshold for the change is about 0.1% to about 10%.

9. The system of claim 8, wherein the processor further acquires at least one location to acquire the discriminatory discrete location image data relative to the region of interest.

10. The system of claim 8, wherein determining at least one path of movement includes determining a plurality of paths of movement.

11. The system of claim 10, wherein comparing the acquired discriminatory discrete location image data to the constructed initial three-dimensional model of the portion of the region of interest includes iteratively comparing the acquired discriminatory discrete location image data to the constructed initial three-dimensional model.

12. The system of claim 10, wherein the plurality of paths of movement includes a plurality of paths covering the same portion of the region of interest.

13. The system of claim 8, wherein acquiring the comparative image data includes acquiring less image data than during acquisition of an initial image data set of the region of interest.

14. The system of claim 8, further comprising:
executing instructions with the processor system to determine a plurality of locations for movement of at least one of the detector or the gantry to acquire a plurality of comparative image data regarding a specific region having a threshold change;
wherein constructing the comparative model includes executing instructions with the processor system to determine differences between the initial three-dimensional model and the plurality of comparative image data acquired.

15. The system of claim 14, wherein the plurality of locations includes an optimal path of movement of the detector relative to the region of interest and based on the specific region having the threshold change.

16. An imaging system for acquiring image data of a subject comprising:
a mobile cart configured to move from a first location to a second location;
a gantry movably attached to the mobile cart and configured to be positioned relative to a region of interest;

a detector moveable with and relative to the gantry to acquire comparative image data;

a tracking system configured to track an instrument position of an instrument and a tracking device connected to the gantry; and a processor configured to execute instructions to:
  acquire selected image data set of the region of interest;
  construct an initial three-dimensional model of at least a portion of the region of interest based on the acquired selected image data set of the region of interest;
  register the initial three-dimensional model to the subject;
  acquire the instrument position of the tracked instrument;
  acquire discriminatory discrete location image data;
  compare the acquired discriminatory discrete location image data to the constructed initial three-dimensional model of the portion of the region of interest;
  determine at least one path of movement of the imaging system to acquire a comparative image data based at least on the acquired the instrument position of the tracked instrument and regarding an identified region having a change between the acquired discriminatory discrete location image data and the constructed initial three-dimensional model;
  acquire the comparative image data by moving the image system along the at least one path; and
  construct a comparative model of the region of interest based on the constructed initial three-dimensional model and the acquired comparative image data;
  wherein the detector is operable to move independently of the gantry and the gantry is operable to move independent of the mobile cart.

17. The imaging system of claim 16, further comprising:
a display to display the constructed comparative model of the region of interest to illustrate changes to the region of interest.

18. The imaging system of claim 16, wherein the gantry encloses a volume and the detector is configured to move within the volume;
  wherein moving the imaging system along the at least one path includes moving the detector alone within the volume or with movement of the gantry along the at least one path.

* * * * *

UNITED STATES PATENT AND TRADEMARK OFFICE
CERTIFICATE OF CORRECTION

PATENT NO. : 12,064,193 B2
APPLICATION NO. : 17/555884
DATED : August 20, 2024
INVENTOR(S) : Patrick A. Helm et al.

It is certified that error appears in the above-identified patent and that said Letters Patent is hereby corrected as shown below:

On the Title Page

Column 1, Related U.S. Application Data, Line 1, Delete "(60)" and insert --(63)-- therefor In the Specification Column 8, Detailed Description, Line 35, Delete "38," and insert --14,-- therefor Column 12, Detailed Description, Line 33, Delete "216" and insert --38-- therefor Column 12, Detailed Description, Line 64, Delete "degrees)(°" and insert --degrees (°)-- therefor Column 13, Detailed Description, Line 49, Delete "12" and insert --10-- therefor Column 13, Detailed Description, Line 52, Delete "12" and insert --10-- therefor Column 13, Detailed Description, Line 53, Delete "12." and insert --10.-- therefor In the Claims Column 19, Claim 2, Line 14, delete "processor:" and insert --processor-- therefor Signed and Sealed this
Twenty-ninth Day of April, 2025

Coke Morgan Stewart
*Acting Director of the United States Patent and Trademark Office*